(12) United States Patent
Gdynia

(10) Patent No.: US 11,072,641 B2
(45) Date of Patent: Jul. 27, 2021

(54) HMGB1 TYROSINE MUTANTS

(71) Applicant: Ruprecht-Karls-Universitaet Heidelberg, Heidelberg (DE)

(72) Inventor: Georg Gdynia, Heidelberg (DE)

(73) Assignee: RUPRECHT-KARLS-UNIVERSITAET HEIDELBERG, Heidelberg (DE)

( * ) Notice: Subject to any disclaimer, the term of this patent is extended or adjusted under 35 U.S.C. 154(b) by 0 days.

(21) Appl. No.: 16/468,475

(22) PCT Filed: Mar. 6, 2017

(86) PCT No.: PCT/EP2017/055216
§ 371 (c)(1),
(2) Date: Jun. 11, 2019

(87) PCT Pub. No.: WO2018/108327
PCT Pub. Date: Jun. 21, 2018

(65) Prior Publication Data
US 2019/0352360 A1 Nov. 21, 2019

(30) Foreign Application Priority Data
Dec. 12, 2016 (WO) .................. PCT/EP2016/080671

(51) Int. Cl.
| | | |
|---|---|---|
| C07K 14/52 | (2006.01) | |
| A61P 35/00 | (2006.01) | |
| A61P 37/02 | (2006.01) | |
| A61K 38/19 | (2006.01) | |
| C12N 15/11 | (2006.01) | |
| A61K 35/17 | (2015.01) | |
| A61K 38/10 | (2006.01) | |
| A61K 38/17 | (2006.01) | |
| A61K 38/00 | (2006.01) | |

(52) U.S. Cl.
CPC .............. *C07K 14/52* (2013.01); *A61K 35/17* (2013.01); *A61K 38/10* (2013.01); *A61K 38/1709* (2013.01); *A61K 38/19* (2013.01); *A61P 35/00* (2018.01); *A61P 37/02* (2018.01); *C12N 15/11* (2013.01); *A61K 38/00* (2013.01)

(58) Field of Classification Search
CPC ................................ C07K 14/52; A61K 38/19
See application file for complete search history.

(56) References Cited

U.S. PATENT DOCUMENTS

| | | | |
|---|---|---|---|
| 6,468,533 | B1 | 10/2002 | Tracey et al. |
| 2003/0144201 | A1 | 7/2003 | Tracey et al. |
| 2011/0123483 | A1 | 5/2011 | Roth et al. |

FOREIGN PATENT DOCUMENTS

| | | |
|---|---|---|
| CA | 2505682 A1 | 6/2004 |
| CA | 2792506 A1 | 9/2011 |
| JP | 2006-506441 A | 2/2006 |
| JP | 2018-538300 A | 12/2018 |
| KR | 10-2008-0011011 A | 1/2008 |
| RU | 2005102593 A | 10/2005 |
| WO | 02/074337 A1 | 9/2002 |
| WO | 2004/004763 A2 | 1/2004 |
| WO | 2004046338 A2 | 6/2004 |
| WO | 2006/024547 A2 | 3/2006 |
| WO | 2008/031612 A1 | 3/2008 |
| WO | 2017098051 A2 | 6/2017 |

OTHER PUBLICATIONS

Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
International Search Report in International Application No. PCT/EP2017/055216, dated Aug. 24, 2017.
International Preliminary Report on Patentability in International Application No. PCT/EP2017/055216, dated Jun. 27, 2019.
Anthis et al., "Beta Integrin Tyrosine Phosphorylation Is a Conserved Mechanism for Regulating Talin-induced Integrin Activation", Journal of Biological Chemistry, vol. 284, No. 52, 2009, pp. 36700-36710.
Gdynia et al., "The HMGB1 protein induces a metabolic type of tumour cell death by blocking aerobic respiration", Nature Communication, vol. 7, Mar. 7, 2016,10764, pp. 1-13.
G. Gdynia "HMGB1 as metabolic weapon in the arsenal of natural killer cells", Pathologe, Berlin, DE, vol. 37, No. 2, Sep. 14, 2016, pp. S169-S172; english abstract on p. S171.
Calogero et al. (1999), Nature genetics 22, 276-280.
Feng and Doolittle J. Mol. Evolution., 25, 351-360, 1987.
G Gdynia: "HMGB1 controls Warburg metabolism in colon cancer cells." Pathologe 2013, Suppl 1, 34, May 26, 2013 (May 6, 2013), pp. 12-12.

(Continued)

Primary Examiner — Zachary C Howard
(74) Attorney, Agent, or Firm — J.A. Lindeman & Co., PLLC

(57) ABSTRACT

The present invention relates to a high mobility group box 1 (HMGB1) polypeptide, wherein in said HMGB1 polypeptide at least one, preferably two, more preferably three, most preferably all four tyrosine residues at positions corresponding to amino acid positions Y109, Y144, Y155 and/or Y162 of human HMGB1 have been exchanged to an amino acid residue independently selected from glutamic acid, glutamine, aspartic acid, asparagine, homoglutamic acid, homoglutamic acid (2-aminohexanedioic acid), and homoglutamine (2,6-diamino-6-oxohexanoic acid). The present invention further relates to a polynucleotide encoding a polypeptide according to the present invention, to a vector comprising said polynucleotide, and to a host cell comprising said polypeptide, said polynucleotide and/or said vector. Also, the present invention relates to methods, kits, and uses related thereto.

14 Claims, 1 Drawing Sheet

Specification includes a Sequence Listing.

(56) References Cited

OTHER PUBLICATIONS

Grundtman et al. (2010), The FASEB journal 24, 570-578.
Higgins et al., CABIOS, 5 1989: 151-153.
Jewett et al. (1996), J Clin Immunol. 16(1):46-54.
Lee et al. (2014), Blood124(2):188.
Liangchun Yang et al: "PKM2 regulates the Warburg effect and promotes HMGB release in sepsis".Nature Communications, vol. 5, Jul. 14, 2014 (Jul. 14, 2014).
H. J. Min et al: "Chaperone-like Activity of High-Mobility Group Box 1 Protein ans Its Role in Reducing the Formation of Polyglutamine Aggregates", The Journal of Immunology, vol. 190, No. 4, Jan. 9, 2013 (Jan. 9, 2013), pp. 179-1806.
Needleman and Wunsch (J. Mol. Biol. 48; 443-453 (1970).
Saidi et al. (2008), PloS one 3, e3601.
Smith and Waterman (Adv. Appl. Math. 2; 482-489 (1981).
Snyder 2004, Pharm Res 21(3): 389-393.
Tey, S-K (2014), Clinical and Translational Immunology 3, e17; doi:10.1038/cti.2014.11.
Walensky 2004, Science 305(5689): 1466-1470.
Martin J Walsh et al: "ML265, a potent PKM2 activator induces tetramerization and reduces tumor formation and size in a mouse xenograft model." Probe Repots from the NIH Molecular Libraries Program, May 8, 2013, pp. 1-3.
Yang et al. (2007), Journal of leukocyte biology 81, 59-66.
Zetterstrom et al., (2002), Pediatric research 52, 148-154.
Taskinen et al., Blood. vol. 112 Issue 11 (2008), p. 980 Abstract 2836.
Carsetti et al., Blood. vol. 112 Issue 11 (2008), p. 980 Abstract 2837.
Cerwenka A. et al., Molecular & Cellular Oncology, vol. 3, No. 4 (Apr. 2016), e1175538.
Alexanian et al., Oncotarget, vol. 5, No. 12, (2014), pp. 4232-4243.

\* cited by examiner

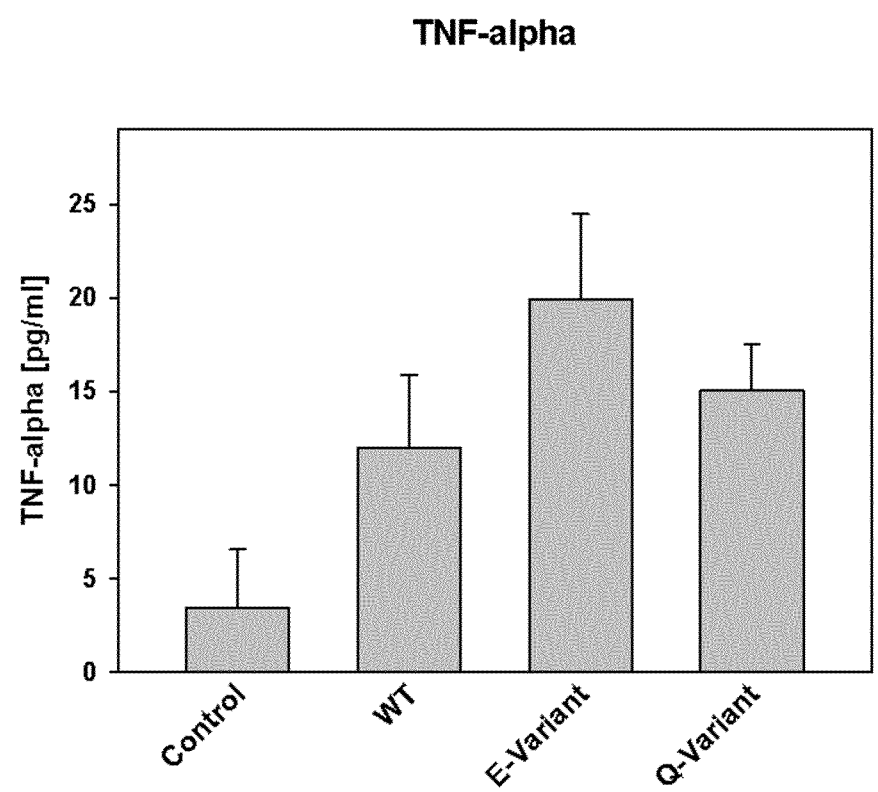

SEQUENCE LISTING

```
<160> NUMBER OF SEQ ID NOS: 8

<210> SEQ ID NO 1
<211> LENGTH: 75
<212> TYPE: PRT
<213> ORGANISM: Homo sapiens

<400> SEQUENCE: 1

Lys Phe Lys Asp Pro Asn Ala Pro Lys Arg Pro Pro Ser Ala Phe Phe
1               5                   10                  15

Leu Phe Cys Ser Glu Tyr Arg Pro Lys Ile Lys Gly Glu His Pro Gly
            20                  25                  30
```

```
Leu Ser Ile Gly Asp Val Ala Lys Lys Leu Gly Glu Met Trp Asn Asn
        35                  40                  45

Thr Ala Asp Asp Lys Gln Pro Tyr Glu Lys Lys Ala Ala Lys Leu
 50                  55                  60

Lys Glu Lys Tyr Glu Lys Asp Ile Ala Ala Tyr
 65                  70                  75

<210> SEQ ID NO 2
<211> LENGTH: 225
<212> TYPE: DNA
<213> ORGANISM: Homo sapiens

<400> SEQUENCE: 2
aagttcaagg atcccaatgc acccaagagg cctccttcgg ccttcttcct cttctgctct      60
gagtatcgcc aaaaatcaa aggagaacat cctggcctgt ccattggtga tgttgcgaag     120
aaactgggag agatgtggaa taacactgct gcagatgaca agcagcctta tgaaaagaag    180
gctgcgaagc tgaaggaaaa atacgaaaag gatattgctg catat                    225

<210> SEQ ID NO 3
<211> LENGTH: 215
<212> TYPE: PRT
<213> ORGANISM: Homo sapiens

<400> SEQUENCE: 3

Met Gly Lys Gly Asp Pro Lys Lys Pro Arg Gly Lys Met Ser Ser Tyr
 1               5                  10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
 50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
            180                 185                 190

Asp Glu Glu Asp Glu Glu Glu Glu Asp Glu Glu Asp Glu Asp Glu
        195                 200                 205

Glu Glu Asp Asp Asp Asp Glu
    210                 215

<210> SEQ ID NO 4
<211> LENGTH: 645
<212> TYPE: DNA
```

<213> ORGANISM: Homo sapiens

<400> SEQUENCE: 4

```
atgggcaaag gagatcctaa gaagccgaga cggaaaatgt catcatatgc attttttgtg      60
caaacttgtc gggaggagca taagaagaag cacccagatg cttcagtcaa cttctcagag     120
ttttctaaga agtgctcaga gaggtggaag accatgtctg ctaaagagaa aggaaaattt     180
gaagatatgg caaagcggac aaggcccgt tatgaaagag aaatgaaaac ctatatccct      240
cccaaagggg agacaaaaaa gaagttcaag gatcccaatg cacccaagag gcctccttcg     300
gccttcttcc tcttctgctc tgagtatcgc ccaaaaatca aggagaaca tcctggcctg      360
tccattggtg atgttgcgaa gaaactggga gagatgtgga ataacactgc tgcagatgac     420
aagcagccct tatgaaagaa ggctgaaaag ctgaaggaaa atacgaaaa ggatattgct       480
gcatatcgag ctaaggaaa gcctgatgca gcaaaaagg gagttgtcaa ggctgaaaaa       540
agcaagaaaa agaaggaaga ggaggaaggt gaggaagatg aagaggatga ggaggaggag     600
gaagatgaag aagatgaaga tgaagaagaa gatgatgatg atgaa                     645
```

<210> SEQ ID NO 5
<211> LENGTH: 75
<212> TYPE: PRT
<213> ORGANISM: Artificial
<220> FEATURE:
<223> OTHER INFORMATION: HMGB1 box B Y-> Q mutein

<400> SEQUENCE: 5

```
Lys Phe Lys Asp Pro Asn Ala Pro Lys Arg Pro Pro Ser Ala Phe Phe
1               5                   10                  15

Leu Phe Cys Ser Glu Gln Arg Pro Lys Ile Lys Gly Glu His Pro Gly
                20                  25                  30

Leu Ser Ile Gly Asp Val Ala Lys Lys Leu Gly Glu Met Trp Asn Asn
            35                  40                  45

Thr Ala Ala Asp Asp Lys Gln Pro Gln Glu Lys Lys Ala Ala Lys Leu
        50                  55                  60

Lys Glu Lys Gln Glu Lys Asp Ile Ala Ala Gln
65                  70                  75
```

<210> SEQ ID NO 6
<211> LENGTH: 215
<212> TYPE: PRT
<213> ORGANISM: Artificial
<220> FEATURE:
<223> OTHER INFORMATION: HMGB1 Y -> Q mutein

<400> SEQUENCE: 6

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
        50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95
```

-continued

```
Arg Pro Pro Ser Ala Phe Phe Leu Phe Cys Ser Glu Gln Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Gln
    130                 135                 140

Glu Lys Lys Ala Ala Lys Leu Lys Glu Lys Gln Lys Asp Ile Ala
145                 150                 155                 160

Ala Gln Arg Ala Lys Gly Lys Pro Asp Ala Lys Lys Gly Val Val
                165                 170                 175

Lys Ala Glu Lys Ser Lys Lys Lys Glu Glu Glu Glu Asp Glu Glu
            180                 185                 190

Asp Glu Glu Asp Glu Glu Glu Glu Asp Glu Glu Asp Glu Asp Glu
        195                 200                 205

Glu Glu Asp Asp Asp Asp Glu
            210                 215

<210> SEQ ID NO 7
<211> LENGTH: 75
<212> TYPE: PRT
<213> ORGANISM: Artificial
<220> FEATURE:
<223> OTHER INFORMATION: Glu-mutein of HMGB1 Box B

<400> SEQUENCE: 7

Lys Phe Lys Asp Pro Asn Ala Pro Lys Arg Pro Pro Ser Ala Phe Phe
1               5                   10                  15

Leu Phe Cys Ser Glu Glu Arg Pro Lys Ile Lys Gly Glu His Pro Gly
            20                  25                  30

Leu Ser Ile Gly Asp Val Ala Lys Lys Leu Gly Glu Met Trp Asn Asn
        35                  40                  45

Thr Ala Ala Asp Asp Lys Gln Pro Glu Glu Lys Ala Ala Lys Leu
    50                  55                  60

Lys Glu Lys Glu Glu Lys Asp Ile Ala Ala Glu
65                  70                  75

<210> SEQ ID NO 8
<211> LENGTH: 215
<212> TYPE: PRT
<213> ORGANISM: Artificial
<220> FEATURE:
<223> OTHER INFORMATION: Glu-mutein of HMGB1

<400> SEQUENCE: 8

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Glu Arg Pro Lys
            100                 105                 110
```

```
Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Glu
    130                 135                 140

Glu Lys Lys Ala Ala Lys Leu Lys Glu Lys Glu Glu Lys Asp Ile Ala
145                 150                 155                 160

Ala Glu Arg Ala Lys Gly Lys Pro Asp Ala Ala Lys Lys Gly Val Val
                165                 170                 175

Lys Ala Glu Lys Ser Lys Lys Lys Lys Glu Glu Glu Asp Glu Glu
                180                 185                 190

Asp Glu Glu Asp Glu Glu Glu Glu Asp Glu Glu Asp Glu Asp Glu Asp Glu
        195                 200                 205

Glu Glu Asp Asp Asp Asp Glu
    210                 215
```

HMGB1 TYROSINE MUTANTS

The present invention relates to a high mobility group box 1 (HMGB1) polypeptide, wherein in said HMGB1 polypeptide at least one, preferably two, more preferably three, most preferably all four tyrosine residues at positions corresponding to amino acid positions Y109, Y144, Y155 and/or Y162 of human HMGB1 have been exchanged to an amino acid residue independently selected from glutamic acid, glutamine, aspartic acid, asparagine, homoglutamic acid (2-aminohexanedioic acid), and homoglutamine (2,6-diamino-6-oxohexanoic acid). The present invention further relates to a polynucleotide encoding a polypeptide according to the present invention, to a vector comprising said polynucleotide, and to a host cell comprising said polypeptide, said polynucleotide and/or said vector. Also, the present invention relates to methods, kits, and uses related thereto.

The High Mobility Group Box 1 (HMGB1) protein belongs to the High Mobility Group (HMG) family of nuclear proteins, which was named due to the unusual high mobility of its members in SDS-polyacrylamide gel-electrophoresis (SDS-PAGE). These proteins are, second to histones, among the most abundant proteins associated with chromatin and they play an architectural role in the nucleus of the eukaryotic cell in that they bend, distort or otherwise modify the conformation of DNA, thereby also modifying the binding of transcription factors to DNA. HMG proteins have been implicated in the genesis of various disorders, like several kinds of benign tumors and autoimmune diseases. Furthermore, the release of high amounts of HMGB1, in particular from NK cells, is pivotal for dendritic cell activation (Saidi et al. (2008), PloS one 3, e3601) and chemotaxis (Yang et al. (2007), Journal of leukocyte biology 81, 59-66). In addition, HMGB1 exhibits striking antimicrobial activity resulting in rapid killing of bacteria (Zetterstrom et al., (2002), Pediatric research 52, 148-154).

Endogenous HMGB1 is also intricately involved in the energy metabolism of cells and organs. HMGB1 knock-out mice are unable to utilize glycogen storage pools in hepatocytes and die due to perinatal hypoglycemia. Glucose temporarily rescues the animals, but the mice succumb several days later due to severe atrophy of inner organs, muscle, and fatty tissue (Calogero et al. (1999), Nature genetics 22, 276-280). Ex vivo incubation of murine muscle tissue with HMGB1 leads to rapid exhaustion of muscle fibers, and elevated HMGB1 concentrations are found in the myoplasm of patients suffering from polymyositis (Grundtman et al. (2010), The FASEB journal 24, 570-578). In summary, both lack and excess of HMGB1 severely affects cellular energy metabolism.

Extracellular HMGB1 is a potent cytokine and a strong activating factor for macrophages and other cells of the immune system, leading to an extensive inflammatory reaction. For this reason, HMGB1 has been implicated in autoimmune diseases such as systemic lupus erythematosus and rheumatoid arthritis. However, high amounts of HMGB1 in blood have also been found to indicate serious or life-threatening inflammatory conditions like sepsis. To antagonize such HMGB1 related pathologies, inhibitors of HMGB1 function, like inhibitory antibodies or fragments thereof, variants of HMGB1 comprising mutations in box A, or polymer conjugates of the box A domain have been described (U.S. Pat. No. 6,468,533, WO 02/074337, US 2003/0144201, WO 2006024547, and WO 2008031612). On the other hand, HMGB1 was proposed as an anti-cancer agent (US 2011/0123483 A1, Gdynia et al. (2016), Nature Communications 7:10764. doi: 10.1038/ncomms10764).

For the HMGB1 proteins, several structural motifs have been described: two DNA-binding domains (box A and box B), two nuclear localization sequences, and a C-terminal acidic domain. The HMGB1 proteins can be extensively posttranslationally modified by acetylation, methylation, ADP-ribosylation, phosphorylation or glycosylation. Acetylation of the nuclear localization sites is the signal that causes the HMGB1 protein to be actively secreted from activated cells of the immune system. Besides active secretion, HMGB1 is also released passively from necrotic cells.

Cancer treatment, besides surgical removal of tumor tissue, essentially relies on the application of medicaments and/or treatments that exert a deleterious function on actively dividing cells. By its nature, such treatment will also harm non-tumor cells and tissues undergoing cell division in the human body, leading to most of the well-known and dreaded side effects of chemo- and radiotherapy, like nausea, digestive distortions, fatigue, hair loss, and more. It is, thus, desirable to have new therapeutic agents at hand that are effective via hitherto unknown routes of action, thereby potentially allowing a dose reduction in chemo- and/or radiotherapy, alleviating side-effects. The provision of such agents using new routes of cancer cell killing could also potentially contribute to the removal of cancer stem cells, which can survive chemotherapy by falling into a resting state and which were recently found to be responsible for at least a fraction of all relapses and metastases.

In recent years, NK cells were found to be of potential use in cancer treatment. The major advantage of NK cells is that they are part of the innate immune system and do not require antigen-specific activation. NK cells can be separated into three major subsets (free, binder, and killer NK cells), based on their ability to bind and kill sensitive target cells (Jewett et al. (1996), J Clin Immunol. 16(1):46-54). The nonbinder, nonkiller NK cells are the most immature and can be activated to become binders and killers, and the ability of NK cells to secrete TNF-alpha was found to correlate with the functional stage of maturation of NK cells (Jewett et al., loc. cit.).

However, as immune-based therapies for cancer become more potent, more effective, and more widely available, optimal management of their potential toxicities becomes increasingly important (Lee et al. (2014), Blood 124(2): 188). In particular, cytokine release syndrome (CRS), a syndrome associated with elevated circulating levels of cytokines, is a potentially life-threatening toxicity that has been observed following administration of natural and bispecific antibodies and, more recently, following T or NK-cell therapies for cancer (Lee et al., loc. cit.).

There is, thus, a need for improved methods of cancer treatment. This problem is solved by the means and methods as disclosed herein below.

Thus, the present invention relates to a high mobility group box 1 (HMGB1) polypeptide, wherein in said HMGB1 polypeptide at least one, preferably two, more preferably three, most preferably all four tyrosine residues at positions corresponding to amino acid positions 22, 57, 68, and 75 of SEQ ID NO: 1 have been exchanged to an amino acid residue independently selected from glutamic acid, glutamine, aspartic acid, asparagine, homoglutamic acid (2-aminohexanedioic acid), and homoglutamine (2,6-diamino-6-oxohexanoic acid).

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which a solely and exclusively consists of B) and to a situation in which, besides B, one or more further elements are present in entity A, such as element C, elements C and D or even further elements.

Further, as used in the following, the terms "preferably", "more preferably", "most preferably", "particularly", "more particularly", "specifically", "more specifically" or similar terms are used in conjunction with optional features, without restricting further possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding further embodiments of the invention, without any restrictions regarding the scope of the invention and without any restriction regarding the possibility of combining the features introduced in such way with other optional or non-optional features of the invention. Moreover, if not noted otherwise, the term "about" relates to the indicated value ±20%.

As used herein, the term "High Mobility Group Box 1 polypeptide" (HMGB1 polypeptide) relates to a member of the high mobility group of polypeptides known to the skilled person, having the modifications as specified in the claims; including partial sequences or derivatives thereof as specified below. Thus, the HMGB1 polypeptide of the present invention, preferably, is not a naturally occurring HMGB1 polypeptide. Also preferably, the HMGB1 polypeptide of the present invention is not human HMGB1, and is not human HMGB1 phosphorylated at amino acids Y109, Y144, Y155 and/or Y162. Preferably, the HMGB1 polypeptide of the present invention has the activity as specified elsewhere herein, preferably cytotoxic activity and/or the activity of activating NK cells, preferably as specified herein in the Examples. Preferably, the HMGB1 polypeptide is a derivative of the human HMGB1 polypeptide (Genbank ACC No: NP_002119.1 GI:4504425, SEQ ID NO: 3). Suitable assays for measuring the activities mentioned before are described in the accompanying Examples. The HMGB1 polypeptide may be purified from cells or tissues or it may be chemically synthesized or, preferably, can be recombinantly manufactured. The HMGB1 polypeptide may comprise further amino acids which may serve as a tag for purification or detection, and/or the HMGB1 polypeptide may be comprised by a fusion polypeptide, as specified elsewhere herein.

Thus, in a preferred embodiment of a polypeptide or peptide of the present invention, the polypeptide or peptide further comprises a detectable tag. The term "detectable tag" refers to a stretch of amino acids which are added to or introduced into the polypeptide or peptide. Preferably, the tag shall be added C- or N-terminally to the polypeptide or peptide; said stretch of amino acids may, e.g., allow for detection of the polypeptide or peptide by an antibody which specifically recognizes the tag or it shall allow for forming a functional conformation, such as a chelator or it shall allow for visualization by fluorescent tags. Preferred tags are the Myc-tag, FLAG-tag, 6-His-tag, HA-tag, GST-tag or GFP-tag. These tags are all well known in the art.

A preferred embodiment of the HMGB1 polypeptide is a polypeptide comprising the B-box motif of the HMGB1 polypeptide, preferably comprising Box B of human HMGB1, more preferably comprising a derivative of SEQ ID NO: 1 with the mutations as specified herein, more preferably comprising a mutated Box B of human HMGB1, preferably as specified herein below.

In the HMGB1 polypeptide of the present invention, at least one, preferably two, more preferably three, most preferably all four tyrosine residues at positions corresponding to amino acid positions 22, 57, 68, and 75 of SEQ ID NO: 1 have been exchanged to an amino acid residue independently selected from glutamic acid, glutamine, aspartic acid, asparagine, homoglutamic acid (2-aminohexanedioic acid), and homoglutamine (2,6-diamino-6-oxohexanoic acid). As is understood by the skilled person, the aforesaid amino acid positions correspond to amino acids Y109, Y144, Y155 and Y162 of human HMGB1 (SEQ ID NO: 3). Preferably, in said HMGB1 polypeptide at least one, preferably two, more preferably three, most preferably all four tyrosine residues at said positions have been exchanged to an amino acid residue independently selected from glutamic acid, glutamine, aspartic acid, and asparagine. More preferably, in said HMGB1 polypeptide at least one, preferably two, more preferably three, most preferably all four tyrosine residues at said positions have been exchanged to glutamic acid residues or have been exchanged to glutamine residues. Even more preferably, in said HMGB1 polypeptide at least one, preferably two, more preferably three, most preferably all four tyrosine residues at said positions have been exchanged to glutamine residues; thus, preferably, the HMGB1 polypeptide preferably comprises the amino acid sequence of SEQ ID NO: 5, more preferably comprises the amino acid sequence of SEQ ID NO: 6. Most preferably, in said HMGB1 polypeptide at least one, preferably two, more preferably three, most preferably all four tyrosine residues at said positions have been exchanged to glutamic acid residues; thus, preferably, the HMGB1 polypeptide preferably comprises the amino acid sequence of SEQ ID NO: 7, more preferably comprises the amino acid sequence of SEQ ID NO: 8.

In an embodiment, the HMGB1 polypeptide or derivative thereof is an oligophosphorylated HMGB1 polypeptide, i.e. an HMGB1 polypeptide in which at least one, preferably two, more preferably three, most preferably all four tyrosine residues has been exchanged for a glutamine, asparagine, or homoglutamine residue(s). In a more preferred embodiment, the HMGB1 polypeptide or derivative thereof is a phosphomimick of an HMGB1 polypeptide, i.e. an HMGB1 polypeptide in which at least one, preferably two, more preferably three, most preferably all four tyrosine residues has been exchanged for a glutamic acid, aspartic acid, or homoglutamic acid residue(s).

Preferably, the HMGB1 polypeptide or a derivative thereof is the HMGB1 polypeptide as specified herein above; the term, preferably, further includes a polypeptide having an amino acid sequence at least 70% identical to the HMGB1 polypeptide or to Box B of the HMGB1 polypeptide as specified herein and having the activity of inducing increased cell death in cancer cells, e.g. in SW480 cell. Thus, preferably, the HMGB1 polypeptide has the activity of inducing increased cell death in cultured SW480 cells at a concentration of 0.8 µM compared to a polypeptide comprising, preferably consisting of an amino acid sequence of SEQ ID NO:3. More preferably, said HMGB1 polypeptide induces increased cell death in cultured SW480 cells at a concentration of 0.8 µM compared to a polypeptide comprising, preferably consisting of an amino acid sequence of SEQ ID NO: 6. Also preferably, the term, preferably, further includes a polypeptide having an amino acid sequence at least 70% identical to the HMGB1 polypeptide or to Box B of the HMGB1 polypeptide as specified herein and having the activity of inducing increased killing of cancer cells by NK cells; more preferably induces increased killing of cultured SW480 cells by NK-92 CI cells at a concentration of 0.8 µM compared to a polypeptide comprising, preferably consisting of an amino acid sequence of SEQ ID NO: 3; more preferably induces increased killing of cultured SW480 cells by NK-92 CI cells at a concentration of 0.8 µM compared to a polypeptide comprising, preferably consisting of an amino acid sequence of SEQ ID NO: 6. Also preferably, the term, preferably, further includes a polypeptide having an amino acid sequence at least 70% identical to the HMGB1 polypeptide or to Box B of the HMGB1 polypeptide as specified herein and having the activity of inducing NK cell maturation, preferably increases tumor necrosis factor alpha (TNF-alpha) secretion by cultured NK-92 CI cells at a concentration of 0.8 µM compared to a polypeptide comprising, preferably consisting of, an amino acid sequence of SEQ ID NO: 3. More preferably, said HMGB1 polypeptide increases tumor necrosis factor alpha (TNF-alpha) secretion by cultured NK-92 CI cells at a concentration of 0.8 µM compared to a polypeptide comprising, preferably consisting of, an amino acid sequence of SEQ ID NO: 6.

The term "TNF-alpha" or "tumor necrosis factor alpha" is known to the skilled person as a cytokine involved in systemic inflammation, in particular in the acute phase reaction. Preferably, TNF-alpha is human TNF-alpha.

Preferably, the HMGB1 polypeptide comprises a nucleic acid sequence having at least 70%, preferably at least 80%, more preferably at least 90%, even more preferably 95%, most preferably at least 98% sequence identity to SEQ ID NO: 1 and/or comprises a nucleic acid sequence having at least 70%, preferably at least 80%, more preferably at least 90%, even more preferably 95%, most preferably at least 98% sequence identity to SEQ ID NO: 3, and, more preferably, has at least one, more preferably at least two, most preferably all three of the aforesaid activities. More preferably, the HMGB1 polypeptide comprises a nucleic acid sequence having at least 70%, preferably at least 80%, more preferably at least 90%, even more preferably 95%, most preferably at least 98% sequence identity to SEQ ID NO: 5 to 8, preferably SEQ ID NO: 6 or 8, and, more preferably, has at least one, more preferably at least two, most preferably all three of the aforesaid activities.

The term "agent providing HMGB1 polypeptide", as used herein, relates to any agent or composition having the capacity of providing or releasing a HMGB1 polypeptide as specified herein to a biological system. Preferably, the agent providing HMGB1 polypeptide is used at a dose inducing a plasma concentration of from 1 nM to 5 µM, more preferably of from 10 nM to 1 µM, most preferably of from 50 nM to 900 nM. Preferably, the term also relates to an agent specifically binding to a tumor cell comprising the HMGB1 polypeptide. Preferably, said agent specifically binding to a tumor cell is an antibody, an aptamer, a lectin, or the like. Also preferably, the term agent providing HMGB1 polypeptide relates to a HMGB1 secreting cell induced to secrete the HMGB1 polypeptide. Cells which can be induced to secrete HMGB1 and methods for doing so are known in the art and include, preferably, the methods as shown in the examples; preferred cells which can be induced to secrete HMGB1 are macrophages and NK cells. Also preferably, the term agent providing HMGB1 polypeptide relates to an expressible polynucleotide encoding the HMGB1 polypeptide. As will be understood by the skilled person, said polynucleotide is, preferably, comprised in a vector or in a host cell, preferably as specified herein below.

The term "derivative", as used in the context of a chemical compound of the present invention, relates to a chemical molecule having a structure related to said chemical compound of the present invention. Preferably, a derivative can be produced from a chemical compound of the present invention by at most three, more preferably at most two, most preferably at most one chemical derivatization reactions. Preferably, the derivative is a compound which is metabolized in a mammalian, preferably a human, body into a chemical compound of the present invention. Also preferably, a derivative is a compound from which a chemical compound of the present invention can be obtained by hydrolysis. In case the chemical compound is a peptide or a polypeptide, the derivative, preferably, is a compound having at least a degree of similarity as specified herein below to the compound it is derived from. As used herein, a derivative of the high mobility group box 1 (HMGB1) polypeptide as specified herein has at least the activity of inhibiting cancer cells as specified herein above.

Preferably, the term "derivative" relating to a polypeptide or peptide includes variants of the amino acid sequence of said polypeptide or peptide, said variants having an amino acid sequence being at least 70%, at least 80%, at least 90%, at least 95%, least 96%, at least 97%, at least 98% or at least 99% identical to the amino acid sequence of the polypeptide or peptide and said variants retaining the function of the polypeptide or peptide as specified herein. The percent identity values are, preferably, calculated over the entire amino acid sequence region. A series of programs based on a variety of algorithms is available to the skilled worker for comparing different sequences. In this context, the algorithms of Needleman and Wunsch or Smith and Waterman give particularly reliable results. To carry out sequence alignments, the program PileUp (J. Mol. Evolution., 25, 351-360, 1987, Higgins et al., CABIOS, 5 1989: 151-153) or the programs Gap and BestFit (Needleman and Wunsch (J. Mol. Biol. 48; 443-453 (1970)) and Smith and Waterman (Adv. Appl. Math. 2; 482-489 (1981)), which are part of the GCG software packet (Genetics Computer Group, 575 Science Drive, Madison, Wis., USA 53711 (1991)), are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000.

Moreover, derivatives of polypeptides or peptides further encompass variants of the aforementioned specific amino acid sequences which may represent orthologs, paralogs or other homologs of the specific polypeptides or peptides. The variants, preferably, comprise an amino acid sequence characterized in that the sequence can be derived from the aforementioned sequences of polypeptides or peptides described above by at least one amino acid substitution and/or addition and/or deletion.

The term derivative also includes chemically modified polypeptides, e.g., polypeptides containing modified amino acids or polypeptides which are, e.g., biotinylated, or are coupled to fluorophores, such as fluorescein, or Cy 3, are conformationally restricted, e.g. by disulfide bridging or by stapling (Walensky 2004, Science 305(5689): 1466-1470), or are linked to cell penetration polypeptides or protein transduction domains (Snyder 2004, Pharm Res 21(3): 389-

393). Such modifications may improve the biological properties of the polypeptides, e.g., cell penetration, binding, stability, or may be used as detection labels.

Preferably, the HMGB1 polypeptide is provided as a pharmaceutically compatible preparation. The terms "pharmaceutically compatible preparation" and "pharmaceutical composition", as used herein, relate to compositions comprising at least one compound of the present invention and optionally one or more pharmaceutically acceptable carrier. The compounds of the present invention can be formulated as pharmaceutically acceptable salts. Preferred acceptable salts are acetate, methylester, HCl, sulfate, chloride and the like. The pharmaceutical compositions are, preferably, administered topically or, more preferably, systemically. Suitable routes of administration conventionally used for drug administration are oral, intravenous, or parenteral administration as well as inhalation. However, depending on the nature and mode of action of a compound, the pharmaceutical compositions may be administered by other routes as well. Moreover, the compounds can be administered in combination with other drugs either in a common pharmaceutical composition or as separated pharmaceutical compositions as specified elsewhere herein, wherein said separated pharmaceutical compositions may be provided in form of a kit of parts.

The compounds are, preferably, administered in conventional dosage forms prepared by combining the drugs with standard pharmaceutical carriers according to conventional procedures. These procedures may involve mixing, granulating and compressing or dissolving the ingredients as appropriate for the desired preparation. It will be appreciated that the form and character of the pharmaceutically acceptable carrier or diluent is dictated by the amount of active ingredient with which it is to be combined, the route of administration and other well-known variables.

The carrier(s) must be acceptable in the sense of being compatible with the other ingredients of the formulation and being not deleterious to the recipient thereof. The pharmaceutical carrier employed may be, for example, a solid, a gel, or a liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl monostearate or glyceryl distearate alone or with a wax. Said suitable carriers comprise those mentioned above and others well known in the art, see, e.g., Remington's Pharmaceutical Sciences, Mack Publishing Company, Easton, Pa.

The diluent(s) is/are selected so as not to affect the biological activity of the compound or compounds. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

A therapeutically effective dose refers to an amount of the compounds to be used in a pharmaceutical composition of the present invention which prevents, ameliorates or treats the symptoms accompanying a disease or condition referred to in this specification. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors; preferably in accordance with any one of the above described methods. As is well known in the medical arts, dosages for any one patient depend upon many factors, including the patient's size, body surface area, age, the particular compound to be administered, sex, time and route of administration, general health, and other drugs being administered concurrently. Progress can be monitored by periodic assessment. A typical dose can be, for example, in the range of 1 to 1000 μg; however, doses below or above this exemplary range are envisioned, especially considering the aforementioned factors. Generally, the regimen as a regular administration of the pharmaceutical composition should be in the range of 1 μg to 10 mg units per day. If the regimen is a continuous infusion, it should also be in the range of 1 μg to 10 mg units per kilogram of body weight per minute, respectively. Progress can be monitored by periodic assessment. Preferred doses and concentrations of the compounds of the present invention are specified elsewhere herein. The pharmaceutical compositions and formulations referred to herein are, preferably, administered at least once in order to treat or ameliorate or prevent a disease or condition recited in this specification. However, the said pharmaceutical compositions may be administered more than one time, for example from one to four times daily up to a non-limited number of days.

Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent, or enclosed or encapsulated in a capsule, sachet, cachet, paper or other suitable containers or vehicles. The resulting formulations are to be adopted to the mode of administration, i.e. in the forms of tablets, capsules, suppositories, solutions, suspensions or the like. Dosage recommendations shall be indicated in the prescribers or users instructions in order to anticipate dose adjustments depending on the considered recipient.

Advantageously, it was found in the work underlying the present invention that the mutated HMGB1 polypeptides of the present invention have increased activities as compared to wildtype HMGB1, with Glu-HMGB1 being still more active than Gln-HMGB1. Further, it was found that by using different mutants of HMGB1, the level of cytotoxicity to cancer cells and of activation of the immune system can be adjusted as needed.

The definitions made above apply mutatis mutandis to the following. Additional definitions and explanations made further below also apply for all embodiments described in this specification mutatis mutandis.

The present invention further relates to a polynucleotide encoding a polypeptide according to the present invention.

The term "polynucleotide", as used herein, relates to a polynucleotide comprising a nucleic acid sequence which encodes a polypeptide having the biological activity as described above, preferably comprising a nucleotide sequence encoding a polypeptide comprising the amino acid sequence of SEQ ID NO: 5 and/or 8 or a derivative thereof as specified herein above. It is to be understood that a polypeptide having an amino acid sequence as detailed above may be encoded due to the degenerated genetic code by more than one species of polynucleotide. Moreover, the term "polynucleotide" as used in accordance with the present invention further encompasses variants of the aforementioned specific polynucleotides. Said variants may represent orthologs, paralogs or other homologs of the polynucleotide of the present invention. The polynucleotide variants, preferably, comprise a nucleic acid sequence characterized in that the sequence can be derived from the aforementioned specific nucleic acid sequences by at least one nucleotide substitution, addition and/or deletion whereby the variant nucleic acid sequence shall still encode a polypeptide having the mutation(s) and activity as specified above. Variants also encompass polynucleotides comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N. Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably, for example, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above.

Alternatively, polynucleotide variants are obtainable by PCR-based techniques such as mixed oligonucleotide primer-based amplification of DNA, i.e. using degenerated primers against conserved domains of the polypeptides of the present invention. Conserved domains of the polypeptides of the present invention may be identified by a sequence comparison of the nucleic acid sequence of the polynucleotide or of the amino acid sequence of the polypeptides as specified above. Suitable PCR conditions are well known in the art. As a template, DNA or cDNA from AAVs may be used. Further, variants include polynucleotides comprising nucleic acid sequences which are at least 70%, at least 75%, at least 80%, at least 85%, at least 90%, at least 95%, at least 98% or at least 99% identical to the nucleic acid sequences detailed above. The percent identity values are, preferably, calculated as set forth above.

A polynucleotide comprising a fragment of any of the aforementioned nucleic acid sequences is also encompassed as a polynucleotide of the present invention. The fragment shall encode a polypeptide which still has the biological activity as specified above. Accordingly, the polypeptide may comprise or consist of the domains of the polypeptide of the present invention conferring the said biological activity. A fragment as meant herein, preferably, comprises at least 50, at least 100, at least 250 or at least 500 consecutive nucleotides of any one of the aforementioned nucleic acid sequences or encodes an amino acid sequence comprising at least 20, at least 30, at least 50, at least 80, at least 100 or at least 150 consecutive amino acids of any one of the aforementioned amino acid sequences.

The polynucleotide of the present invention shall be provided, preferably, either as an isolated polynucleotide (i.e. isolated from its natural context) or in genetically modified form. The polynucleotide, preferably, is DNA including cDNA or RNA. The term encompasses single as well as double stranded polynucleotides. Moreover, comprised are also chemically modified polynucleotides including naturally occurring modified polynucleotides such as glycosylated or methylated polynucleotides or artificially modified ones such as biotinylated polynucleotides.

The polynucleotides of the present invention either essentially consist of the aforementioned nucleic acid sequences or comprise the aforementioned nucleic acid sequences. Thus, they may contain further nucleic acid sequences as well. Specifically, the present invention also relates to a vector comprising the polynucleotide of the present invention.

The present invention further relates to a vector comprising the polynucleotide according to the present invention.

The term "vector", preferably, encompasses phage, plasmid, viral or retroviral vectors as well as artificial chromosomes, such as bacterial or yeast artificial chromosomes. More preferably, the term relates to a vector derived from a virus, said virus, preferably, preferentially infecting tumor cells (tumorotropic virus) or a virus preferentially lysing cancer cells (oncolytic virus). Moreover, the term also relates to targeting constructs which allow for random or site-directed integration of the targeting construct into genomic DNA. Such targeting constructs, preferably, comprise DNA of sufficient length for either homologous or heterologous recombination. The vector encompassing the polynucleotide of the present invention, preferably, further comprises selectable markers for propagation and/or selection in a host. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerens. Alternatively, a plasmid vector may be introduced by heat shock or electroporation techniques. Should the vector be a virus, it may be packaged in vitro using an appropriate packaging cell line prior to application to host cells. Viral vectors may be replication competent or replication defective.

Preferably, in the vector of the invention the polynucleotide of the invention is operatively linked to expression control sequences allowing expression in prokaryotic or eukaryotic cells or isolated fractions thereof. Expression of said polynucleotide comprises transcription of the polynucleotide, preferably into a translatable mRNA. Regulatory elements ensuring expression in eukaryotic cells, preferably mammalian cells, are well known in the art. They, preferably, comprise regulatory sequences ensuring initiation of transcription and, optionally, poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Moreover, inducible expression control sequences may be used in an expression vector encompassed by the present invention. Such inducible vectors may, preferably, comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pBluescript (Stratagene), pCDM8, pRc/CMV, pcDNA1, pcDNA3 (InVitrogene) or pSPORT1 (GIBCO BRL). Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994).

Further, the present invention relates to a host cell comprising the polypeptide, the polynucleotide and/or the vector according to the present invention.

The term "host cell", preferably, relates to a cell compatible with being administered to a subject. More preferably, said cell is immunologically compatible with the subject. Most preferably, the cell is a cell which was obtained from said subject. The host cell of the current invention, preferably, is a cell with a tendency to migrate into the vicinity of cancer cells, More preferably, the host cell is an immune cell, and most preferably is a cell of the immune system specifically recognizing a tumor specific antigen, like, e.g. a tumor antigen specific T-cell.

Moreover, the host cell comprising the polynucleotide or vector of the present invention, preferably, is a cell capable of producing a HMGB1 polypeptide of the present invention, e.g. a bacterial, yeast, insect, or a mammalian cell.

The present invention further relates to a polypeptide, a polynucleotide, a vector, and/or a host cell according to the present invention for use as a medicament.

Also, the present invention relates to a polypeptide, a polynucleotide, a vector, and/or a host cell according to the present invention for use in treating cancer and/or in immune modulation.

The term "cancer", as used herein, refers to a disease of an animal, preferably man, characterized by inappropriate and/or uncontrolled growth by a group of body cells. This uncontrolled growth may be accompanied by intrusion into and destruction of surrounding tissue and possibly spread of inappropriately proliferating cells to other locations in the body. Thus, preferably, the polynucleotide, vector, and/or host cell according to the present invention are for use in the treatment of cancer.

Preferably, the cancer is selected from the list consisting of acute lymphoblastic leukemia, acute myeloid leukemia, adrenocortical carcinoma, aids-related lymphoma, anal cancer, appendix cancer, astrocytoma, atypical teratoid, basal cell carcinoma, bile duct cancer, bladder cancer, brain stem glioma, breast cancer, Burkitt lymphoma, carcinoid tumor, cerebellar astrocytoma, cervical cancer, chordoma, chronic lymphocytic leukemia, chronic myelogenous leukemia, colon cancer, colorectal cancer, craniopharyngioma, endometrial cancer, ependymoblastoma, ependymoma, esophageal cancer, extracranial germ cell tumor, extragonadal germ cell tumor, extrahepatic bile duct cancer, gallbladder cancer, gastric cancer, gastrointestinal stromal tumor, gestational trophoblastic tumor, hairy cell leukemia, head and neck cancer, hepatocellular cancer, Hodgkin lymphoma, hypopharyngeal cancer, hypothalamic and visual pathway glioma, intraocular melanoma, Kaposi sarcoma, laryngeal cancer, medulloblastoma, medulloepithelioma, melanoma, Merkel cell carcinoma, mesothelioma, mouth cancer, multiple endocrine neoplasia syndrome, multiple myeloma, mycosis fungoides, nasal cavity and paranasal sinus cancer, nasopharyngeal cancer, neuroblastoma, neuroendocrine tumor (NET)/carcinoma, non-hodgkin lymphoma, non-small cell lung cancer, oral cancer, oropharyngeal cancer, osteosarcoma, ovarian cancer, ovarian epithelial cancer, ovarian germ cell tumor, ovarian low malignant potential tumor, pancreatic cancer, papillomatosis, paranasal sinus and nasal cavity cancer, parathyroid cancer, penile cancer, pharyngeal cancer, pheochromocytoma, pituitary tumor, pleuropulmonary blastoma, primary central nervous system lymphoma, prostate cancer, rectal cancer, renal cell cancer, retinoblastoma, rhabdomyosarcoma, salivary gland cancer, sézary syndrome, small cell lung cancer, small intestine cancer, soft tissue sarcoma, squamous cell carcinoma, squamous neck cancer, testicular cancer, throat cancer, thymic carcinoma, thymoma, thyroid cancer, urethral cancer, uterine sarcoma, vaginal cancer, vulvar cancer, Waldenström macroglobulinemia, and wilms tumor.

More preferably, the cancer is leukemia, lymphoma, HPV-related cancer, colorectal carcinoma, gastric cancer, pancreas cancer, lung cancer, brain cancer, or breast cancer. A preferred colorectal carcinoma is colon carcinoma. Even more preferably, the cancer is leukemia, most preferably chronic lymphocytic leukemia (CLL).

The term "cancer therapy" includes all means and methods known to the skilled person to be suitable in treating cancer. Preferably, the term relates to therapies approved for cancer treatment in humans. The term "cellular cancer immune therapy", preferably relates to a method of cancer treatment comprising administration of cells, preferably autologous cells, to a subject, e.g. preferably, B-cells, T-cells, and/or NK cells, or predecessor cells thereof, e.g. hematopoietic stem cells. Preferably, said cells administered are NK cells or predecessor cells thereof. More preferably, said cells are tumor-recognizing NK cells or predecessor cells thereof. Even more preferably, said cells are tumor-recognizing NK cells, most preferably are autologous tumor-recognizing NK cells.

Preferably, treating cancer and immune modulation comprise cellular cancer immune therapy. Also preferably, treating cancer and/or in immune modulation comprises inducing TNF-alpha secretion by NK cells, preferably is inducing NK cell maturation. Also preferably, treating cancer and/or in immune modulation comprises avoiding inducing adverse events, more preferably comprises avoiding inducing cytokine release syndrome (CRS).

The terms "natural killer cells" and "NK cells" are known to the skilled person to relate to cytotoxic lymphocytes which are part of the innate immune system and which, by receptors including NKG2D, NKp44, NKp46, NKp30, and others, recognize a number of ligands, including ULBP and MICA, which are typically expressed on tumor cells. The term "NK cell maturation" is understood by the skilled person. Preferably, NK cell maturation is an increase of the fraction of NK cells binding and/or killing tumor cells in the total fraction of NK cells.

"Adverse events" related to HMGB1 treatment and to cellular immune therapy, as well as markers and symptoms thereof and suitable treatments are known to the skilled person (e.g. as reviewed in Tey, S-K (2014), Clinical and Translational Immunology 3, e17; doi:10.1038/cti.2014.11). Adverse events include, preferably, neurotoxicity (causing, e.g., hearing loss, seizures, or coma), vitiligo, colitis, raised liver enzymes, acute pulmonary infiltrates, B-cell depletion, hypogammaglobulinaemia, and cytokine release syndrome. The term "cytokine release syndrome" and its symptoms and markers are known to the skilled person, e.g. from Lee et al. (loc. cit.). Preferably, the marker for prevalent or impeding CRS a C-reactive protein, IL-6, and/or TNF-alpha, preferably the marker is TNF-alpha.

Further, the present invention relates to a method for treating cancer and/or for inducing immune modulation in a subject comprising
a) contacting said subject to a polypeptide according to any one of embodiments 1 to 18, a polynucleotide according to embodiment 19, a vector according to embodiment 20, and/or a host cell according to embodiment 21, and, thereby
b) treating cancer and/or inducing immune modulation in said subject.

The methods of the present invention, preferably, are in vivo methods. Moreover, they may comprise steps in addition to those explicitly mentioned above. For example, a further step of the method for treating cancer and/or for inducing immune modulation may relate, e.g., to surgically removing tumor tissue before or after administration of said pharmaceutically active compounds. Preferably, the methods are performed with the steps performed in the order indicated. Moreover, one or more of said steps may be performed by automated equipment.

The term "subject", as used herein, relates to an animal, preferably a farm or companion animal, more preferably a mammal, most preferably a human. Preferably, the subject is a subject suffering from cancer, more preferably as specified above.

The term "treating" refers to ameliorating the diseases or disorders referred to herein or the symptoms accompanied therewith to a significant extent. Said treating as used herein also includes, preferably, an entire restoration of the health with respect to the diseases or disorders referred to herein. It is to be understood that treating as used in accordance with the present invention may not be effective in all subjects to be treated. However, the term shall, preferably, require that a statistically significant portion of subjects suffering from a disease or disorder referred to herein can be successfully treated. Whether a portion is statistically significant can be determined without further ado by the person skilled in the art using various well known statistic evaluation tools, e.g., determination of confidence intervals, p-value determination, Student's t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the treatment shall be effective for at least 60%, at least 70%, at least 80%, or at least 90% of the subjects of a given cohort or population.

The term "immune modulation" as used herein, relates to inducing a change in the extent the immune system of a subject reacts to an antigen. Preferably, the immune modulation is an activation. Preferably, the antigen is a tumor antigen, more preferably a tumor-specific antigen, i.e., preferably, an antigen expressed and/or presented only by tumor cells of the subject. More preferably, modulating the immune response of a subject is inducing TNF-alpha secretion by NK cells, most preferably is inducing NK cell maturation, preferably as specified above.

The present invention further relates to a method for providing HMGB1 treatment to a subject avoiding inducing an adverse event, preferably avoiding inducing cytokine release syndrome (CRS) comprising
a) administering an agent providing HMGB1 to said subject
b) determining at least one parameter of adverse events, preferably of CRS in a sample of said patient,
c) continuing administration of an agent providing HMGB1 with an alternative agent providing HMGB1,
wherein said alternative agent providing HMGB1 provides a HMGB1 polypeptide with a decreased activity in inducing TNF-alpha secretion and/or a decreased activity in inducing killing of cells by NK cells in case said parameter determined in step b) is indicative of an increased probability of an adverse event, preferably CRS; and/or
wherein said alternative agent providing HMGB1 provides a HMGB1 polypeptide with an increased activity in inducing TNF-alpha secretion and/or a decreased activity in inducing killing of cells by NK cells in case said parameter determined in step b) is indicative of a low probability of an adverse event, preferably CRS;
d) thereby providing HMGB1 treatment to a subject avoiding an adverse event, preferably avoiding inducing CRS.

Preferably, the HMGB1 polypeptide with a decreased activity in inducing TNF-alpha secretion and/or a decreased activity in inducing killing of cells by NK cells is the HMGB1 polypeptide of embodiment 5, preferably a polypeptide comprising the amino acid sequence of SEQ ID NO: 5 or 6. Also preferably, the HMGB1 polypeptide with an increased activity in inducing TNF-alpha secretion and/or an increased activity in inducing killing of cells by NK cells is the HMGB1 polypeptide of embodiment 4, preferably a polypeptide comprising the amino acid sequence of SEQ ID NO: 7 or 8. Preferably, the parameter of CRS is TNF-alpha concentration.

Further, the present invention relates to a method for modulating the immune response of a subject, comprising
a) administering an agent providing a HMGB1 polypeptide to said subject, wherein said HMGB1 polypeptide is a polypeptide according to the present invention, and, thereby
b) modulating the immune response of said subject.

Preferably, said modulating the immune response of a subject is inducing TNF-alpha secretion by NK cells, preferably is inducing NK cell maturation, preferably as specified herein above Also, the present invention relates to a kit comprising a polypeptide, a polynucleotide, a vector, and/or a host cell according to the present invention in a housing.

The term "kit" as used herein refers to a collection comprising at least the aforementioned means, provided separately or combined, preferably within a single container. The container, also preferably, further comprises instructions for carrying out the method of the present invention. The components of the kit are provided, preferably, in a "ready-to-use" manner, e.g., concentrations are adjusted accordingly, etc. Preferably, the further comprises natural killer cells (NK cells) and/or a means for the isolation thereof. Means for the isolation of NK cells are means for specific use in the isolation of NK cells and include in particular antibodies specifically binding to NK cells.

In view of the above, the following embodiments are preferred:
1. A high mobility group box 1 (HMGB1) polypeptide, wherein in said HMGB1 polypeptide at least one, preferably two, more preferably three, most preferably all four tyrosine residues at positions corresponding to amino acid positions 22, 57, 68, and 75 of SEQ ID NO: 1 have been exchanged to an amino acid residue independently selected from glutamic acid, glutamine, aspartic acid, asparagine, homoglutamic acid (2-aminohexanedioic acid), and homoglutamine (2,6-diamino-6-oxohexanoic acid).
2. The HMGB1 polypeptide of embodiment 1, wherein in said HMGB1 polypeptide at least one, preferably two, more preferably three, most preferably all four tyrosine residues at said positions have been exchanged to an amino acid residue independently selected from glutamic acid, glutamine, aspartic acid, and asparagine.
3. The HMGB1 polypeptide of embodiment 1 or 2, wherein in said HMGB1 polypeptide at least one, preferably two, more preferably three, most preferably all four tyrosine residues at said positions have been exchanged to glutamic acid residues or have been exchanged to glutamine residues.
4. The HMGB1 polypeptide of any one of embodiments 1 to 3, wherein in said HMGB1 polypeptide at least one, preferably two, more preferably three, most preferably all four tyrosine residues at said positions have been exchanged to glutamic acid residues.
5. The HMGB1 polypeptide of any one of embodiments 1 to 4, wherein in said HMGB1 polypeptide at least one, preferably two, more preferably three, most preferably all four tyrosine residues at said positions have been exchanged to glutamine residues.
6. The HMGB1 polypeptide of any one of embodiments 1 to 5, wherein said HMGB1 polypeptide comprises a nucleic acid sequence having at least 70%, preferably at least 80%, more preferably at least 90%, even more preferably 95%, most preferably at least 98% sequence identity to SEQ ID NO: 1 and/or comprises a nucleic acid sequence having at least 70%, preferably at least 80%, more preferably at least 90%, even more preferably 95%, most preferably at least 98% sequence identity to SEQ ID NO: 3.
7. The HMGB1 polypeptide of any one of embodiments 1 to 6, wherein said HMGB1 polypeptide comprises a nucleic acid sequence having at least 70%, preferably at least 80%, more preferably at least 90%, even more preferably 95%, most preferably at least 98% sequence identity to SEQ ID NO: 5 to 8, preferably SEQ ID NO: 6 or 8, preferably comprises the nucleic acid sequence of SEQ ID NO: 5 to 8, preferably of SEQ ID NO: 6 or 8.
8. The HMGB1 polypeptide of any one of embodiments 1 to 7, wherein said HMGB1 polypeptide is derived from a human HMGB1 polypeptide.
9. The HMGB1 polypeptide of any one of embodiments 1 to 8, wherein said HMGB1 polypeptide is non-naturally occurring.
10. The HMGB1 polypeptide of any one of embodiments 1 to 9, wherein said HMGB1 polypeptide induces increased cell death in cultured SW480 cells at a concentration of 0.8 µM compared to a polypeptide comprising, preferably consisting of an amino acid sequence of SEQ ID NO:3.
11. The HMGB1 polypeptide of any one of embodiments 1 to 10, wherein said HMGB1 polypeptide induces increased cell death in cultured SW480 cells at a concentration of 0.8 µM compared to a polypeptide comprising, preferably consisting of an amino acid sequence of SEQ ID NO: 6.
12. The HMGB1 polypeptide of any one of embodiments 1 to 11, wherein said cell death is increased by at least 10%, preferably at least 20%, more preferably at least 30%, more preferably at least 40%.
13. The HMGB1 polypeptide of any one of embodiments 1 to 12, wherein said HMGB1 polypeptide induces increased killing of cultured SW480 cells by NK-92 CI cells at a concentration of 0.8 µM compared to a polypeptide comprising, preferably consisting of an amino acid sequence of SEQ ID NO: 3.
14. The HMGB1 polypeptide of any one of embodiments 1 to 13, wherein said HMGB1 polypeptide induces increased killing of cultured SW480 cells by NK-92 CI cells at a concentration of 0.8 µM compared to a polypeptide comprising, preferably consisting of an amino acid sequence of SEQ ID NO: 6.
15. The HMGB1 polypeptide of any one of embodiments 1 to 14, wherein said killing is increased by at least 5%, preferably at least 10%, more preferably at least 15%, most preferably at least 20%.
16. The HMGB1 polypeptide of any one of embodiments 1 to 15, wherein said HMGB1 polypeptide increases tumor necrosis factor alpha (TNF-alpha) secretion by cultured NK-92 CI cells at a concentration of 0.8 µM compared to a polypeptide comprising, preferably consisting of, an amino acid sequence of SEQ ID NO: 3.
17. The HMGB1 polypeptide of any one of embodiments 1 to 16, wherein said HMGB1 polypeptide increases tumor necrosis factor alpha (TNF-alpha) secretion by cultured NK-92 CI cells at a concentration of 0.8 µM compared to a polypeptide comprising, preferably consisting of, an amino acid sequence of SEQ ID NO: 6.
18. The HMGB1 polypeptide of any one of embodiments 1 to 17, wherein said TNF-alpha secretion is increased by at least 10% preferably at least 20%, more preferably at least 30%, even more preferably at least 40%, most preferably at least 50%.
19. A polynucleotide encoding a polypeptide according to any one of embodiments 2 to 18.
20. A vector comprising the polynucleotide according to embodiment 19.
21. A host cell comprising the polypeptide according to any one of embodiments 1 to 18, the polynucleotide according to embodiment 19 and/or the vector according to embodiment 20.
22. A polypeptide according to any one of embodiments 1 to 18, a polynucleotide according to embodiment 19, a vector according to embodiment 20, and/or a host cell according to embodiment 21 for use as a medicament.
23. A polypeptide according to any one of embodiments 1 to 18, a polynucleotide according to embodiment 19, a vector according to embodiment 20, and/or a host cell according to embodiment 21 for use in treating cancer and/or in immune modulation.
24. The polypeptide, polynucleotide, vector, and/or host cell of embodiment 23, wherein said use in treating cancer and in immune modulation comprises cellular cancer immune therapy.
25. The polypeptide, polynucleotide, vector, and/or host cell of embodiment 23, wherein said use in treating cancer and/or in immune modulation comprises inducing TNF-alpha secretion by NK cells, preferably is inducing NK cell maturation.
26. The polypeptide, polynucleotide, vector, and/or host cell of embodiment 23, wherein said use in treating cancer and/or in immune modulation comprises avoiding inducing an adverse event, preferably comprises avoiding inducing cytokine release syndrome (CRS).

27. A method for treating cancer and/or for inducing immune modulation in a subject comprising
a) contacting said subject to a polypeptide according to any one of embodiments 1 to 18, a polynucleotide according to embodiment 19, a vector according to embodiment 20, and/or a host cell according to embodiment 21, and, thereby
b) treating cancer and/or inducing immune modulation in said subject.

28. A method for providing HMGB1 treatment to a subject avoiding inducing an adverse event, preferably avoiding inducing cytokine release syndrome (CRS) comprising
a) administering an agent providing HMGB1 to said subject
b) determining at least one parameter of adverse events, preferably of CRS in a sample of said patient,
c) continuing administration of an agent providing HMGB1 with an alternative agent providing HMGB1,
wherein said alternative agent providing HMGB1 provides a HMGB1 polypeptide with a decreased activity in inducing TNF-alpha secretion and/or a decreased activity in inducing killing of cells by NK cells in case said parameter determined in step b) is indicative of an increased probability of an adverse event, preferably CRS; and/or
wherein said alternative agent providing HMGB1 provides a HMGB1 polypeptide with an increased activity in inducing TNF-alpha secretion and/or a decreased activity in inducing killing of cells by NK cells in case said parameter determined in step b) is indicative of a low probability of an adverse event, preferably CRS;
d) thereby providing HMGB1 treatment to a subject avoiding an adverse event, preferably avoiding inducing CRS.

29. The method of embodiment 28, wherein said HMGB1 polypeptide with a decreased activity in inducing TNF-alpha secretion and/or a decreased activity in inducing killing of cells by NK cells is the HMGB1 polypeptide of embodiment 5.

30. The method of embodiment 28 or 29, wherein said HMGB1 polypeptide with an increased activity in inducing TNF-alpha secretion and/or an increased activity in inducing killing of cells by NK cells is the HMGB1 polypeptide of embodiment 4.

31. The method of any one of embodiments 28 to 30, wherein said parameter of CRS is TNF-alpha concentration.

32. A method for modulating the immune response of a subject, comprising
a) administering an agent providing a HMGB1 polypeptide to said subject, wherein said HMGB1 polypeptide is a polypeptide according to any one of embodiment 1 to 18, and, thereby
b) modulating the immune response of said subject.

33. The method of embodiment 32, wherein said modulating the immune response of a subject is inducing TNF-alpha secretion by NK cells, preferably is inducing NK cell maturation.

34. A kit comprising a polypeptide according to any one of embodiments 1 to 18, a polynucleotide according to embodiment 19, a vector according to embodiment 20, and/or a host cell according to embodiment 21 in a housing.

35. The kit of embodiment 34, wherein said kit further comprises natural killer cells (NK cells) and/or a means for the isolation thereof.

36. The kit of embodiment 34 or 35, wherein said killer cells are tumor-recognizing NK cells.

37. Use of a polypeptide according to any one of embodiments 1 to 18, a polynucleotide according to embodiment 19, a vector according to embodiment 20, and/or a host cell according to embodiment 21 for the manufacture of a medicament, preferably a medicament for treating cancer and/or for immune modulation.

All references cited in this specification are herewith incorporated by reference with respect to their entire disclosure content and the disclosure content specifically mentioned in this specification.

FIGURE LEGENDS

FIG. 1: Potent activation of Natural Killer cells (NK-92 CI) by Glu-HMGB1 (n=3, p<0.05). WT=HMGB1 WT, E-Variant=Glu-HMGB1 (SEQ ID NO: 8), Q-Variant=Gln-HMGB1 (SEQ ID NO: 6).

The following Examples shall merely illustrate the invention. They shall not be construed, whatsoever, to limit the scope of the invention.

EXAMPLE 1: METHODS

Cr-51 Release Assay

SW480 colon cancer cells were cultured in 96-well plates (20000 cells/well) and labeled with $^{51}$Cr (25 µCi/well) for 2 h. Then cells were treated with HMGB1 and NK-cells for 24 h hours. Medium was removed and counted for radioactivity (cpm1). Cells were washed 4× with medium and solubilized with 100 µl 0.5N NaOH. The lysates were counted for radioactivity (cpm2).

Radioactivity Counting

Samples were mixed with 10 ml UltimaGold and counted in a liquid scintillation counter.

$$\text{Calculation of cell death: } \frac{cpm1}{cpm1 + cpm2} \times 100 = \% \text{ cell death.}$$

Generation of GluHMGB1, GlnHMGB1 and Wildtype HMGB1

Plasmids encoding a HMGB1 polypeptide with all four B-Box domain tyrosine residues replaced by glutamate or glutamine residues, respectively, were transfected into HEK cells (serum-free suspension cell culture, 1,000 ml (app. 2.5×10$^6$ cells/ml), then supplemented with Valproic Acid). For generation of wildtype HMGB1, the B-Box domain was unmodified on its tyrosine residues. The cell pellet was homogenized and purified via IMAC and TALON (Clontech) Resins and eluted using imidazole. 15 eluates were analyzed via SDS-PAGE (Coomassie staining). After pooling of positive eluates the protein was gel filtrated (Superdex) and finally analyzed by SDS-PAGE. 800 nM of the purified protein was used in the experiments.

Activation of NK Cells

Activation of Natural Killer cell line NK-92 CI was measured by detection of TNF-alpha release into the supernatant using 400,000 NK cells stimulated with 800 nM of the indicated HMGB1 protein for 24 h. Detection of TNF-alpha was performed with an ELISA-Kit (Avia Systems Biology, Catalog No. OKAA00027_96 W) according to the instructions of the manufacturer.

EXAMPLE 2: RESULTS AND DISCUSSION

Different HMGB1 Forms Display Both Distinct Cytotoxicity Towards Cancer Cells and Differences in Enhancement of Natural Killer Cytotoxicity Towards Cancer Cells and Activation of NK Cells Using both a very short time period for assessment of HMGB1 cytotoxicty of 24 h and the highly sensitive $^{51}$Cr (chromium 51) release goldstandard assay for detection of cell death, we revealed surprising new cytotoxicity profiles of different HMGB1 forms, modified on their B-Box domain. Gln-HMGB1 showed 43% more cell death towards cancer cells compared to wildtype HMGB1 whereas Glu-HMGB1 showed even 83% more cell death compared to wildtype HMGB1 (Table 1).

Next, effector (E) cells (NK-92 CI Natural Killer cell line) were incubated with $^{51}$Cr labeled target (T) cells (SW480 colon cancer cells) at various E:T ratios: 5:1, 10:1 and 20:1 (Table 1). Gln-HMGB1 plus NK cells showed up to 55% more cell death towards cancer cells compared to NK cell lytic activity with no stimulation whereas Glu-HMGB1 showed up to 94% more cell death towards cancer cells compared to NK cell lytic activity with no stimulation (E:T 5:1 respectively) (Table 1). Further, Gln-HMGB1 plus NK cells showed up to 13% more cell death towards cancer cells compared to NK cell lytic activity after stimulation with wildtype HMGB1 whereas Glu-HMGB1 showed up to 25% more cell death towards cancer cells compared to NK cell lytic activity after stimulation with wildtype HMGB1 (E:T 5:1 respectively) (Table 1).

In summary the three different HMGB1 isoforms display distinct cytotoxicity profiles. Glu-HMGB1 is superior to both wildtype HMGB1 and Gln-HMGB1 regarding cytotoxicity towards cancer cells and regarding enhancement of NK cell lytic activity towards cancer cells. Gln-HMGB1 is superior to wildtype HMGB1 regarding cytotoxicity towards cancer cells and regarding enhancement of NK cell lytic activity towards cancer cells. Thus wildtype HMGB1 displays the poorest cytotoxicity profile compared to Glu-HMGB1 and Gln-HMGB1. Gln-HMGB1 still exerts strong cytotoxicity towards cancer cells (albeit less than Glu-HMGB1) with a moderate enhancement of NK cell lytic activity (ranging in between wildtype HMGB1 (low NK cell lytic activity) and Glu-HMGB1 (high NK cell lytic activity)).

Moreover, the three different HMGB1 isoforms display distinct activities in activating NK cells. We measured the secretion of tumor necrosis factor-alpha (TNF-alpha) by NK-92 CI cells following activation by HMGB1 stimulation. Glu-HMGB1 most potently stimulated secretion of TNF-alpha and thus most potently activated NK cells to become binders and killers.

Thus by the application of different forms of HMGB1, Glu-HMGB1 and Gln-HMGB1, in cancer therapy it is possible to regulate (i) direct cytotoxicity towards cancer cells, (ii) NK cell cytotoxicity towards cancer cells that are in the vicinity of the tumor and (iii) overall activation of circulating NK cells (switching them to binders and killers) and thus facilitating recruitment of NK cells to the tumor. The results shown herein demonstrate that Glu-HMGB1 and Gln-HMGB1 on its own or combined with cellular immune therapies (e.g. NK cells) display augmented cytotoxicity towards cancer cells compared to wildtype HMGB1.

With GluHMGB1 and GlnHMGB1 the clinician has a tool by which he can regulate the general activation of the immune system (e.g. activation of NK cells secreting different cytokines, e.g. TNF-alpha) during HMGB1 based cancer therapy. Depending on the desired activation status or desired cytokine blood plasma levels (e.g. TNF-alpha), Glu-HMGB1 could be used for strong activation of the immune system and enhanced cytokine release while Gln-HMGB1 could be used for a moderate activation of the immune system and moderate cytokine release (e.g. from NK cells). By combining both, Glu-HMGB1 and Gln-HMGB1, one could enhance or decrease the release of cytokines while always having increased direct cytotoxicity towards cancer cells, and NK cell cytotoxicity towards cancer cells that are in the vicinity of the tumor, compared to wildtype HMGB1.

TABLE 1

Cr-51 release assay using NK-92 CI Natural Killer cells and SW480 colon cancer cells plus HMGB1 (n = 3, *p < 0.05).

| NK cells | HMGB1 | % Cell death (mean, N = 3) | % Cell death (SD) | % Increased cell death compared to WT | % Increased cell death compared to only NK cells | % Increased cell death compared to WT plus NK cells |
|---|---|---|---|---|---|---|
| 0 | Control | 0.45 | 0.21 | | | |
| 100000 | Control | 8.05 | 1.06 | | 0 | |
| 200000 | Control | 28.29 | 1.08 | | 0 | |
| 400000 | Control | 56.41 | 2.27 | | 0 | |
| 0 | HMGB1_WT | 3.95 | 0.35 | 0 | | |
| 0 | HMGB1_Q | 5.67 | 0.57 | 43* | | |
| 0 | HMGB1_E | 7.23 | 0.21 | 83* | | |
| 100000 | HMGB1_WT | 10.98 | 0.04 | | 36* | 0 |
| 100000 | HMGB1_Q | 12.45 | 0.71 | | 55* | 13* |
| 100000 | HMGB1_E | 15.59 | 0.21 | | 94* | 25* |
| 200000 | HMGB1_WT | 31.87 | 1.36 | | 13* | 0 |
| 200000 | HMGB1_Q | 35.56 | 0.20 | | 26* | 12* |
| 200000 | HMGB1_E | 38.48 | 1.38 | | 36* | 21* |
| 400000 | HMGB1_WT | 58.81 | 1.73 | | 4* | 0 |
| 400000 | HMGB1_Q | 62.55 | 0.54 | | 11* | 6* |
| 400000 | HMGB1_E | 69.21 | 3.54 | | 23* | 18* |

The invention claimed is:

1. A high mobility group box 1 (HMGB1) polypeptide, wherein in said HMGB1 polypeptide, at least one tyrosine residue at a position corresponding to one of amino acid positions 22, 57, 68, and 75 of SEQ ID NO: 1 has been exchanged to an amino acid residue independently selected from glutamic acid, glutamine, aspartic acid, asparagine, homoglutamic acid (2-aminohexanedioic acid), and homoglutamine (2,6-diamino-6-oxohexanoic acid), and wherein said HMGB1 polypeptide otherwise comprises an amino acid sequence having at least 95%, at least 98% or 100% sequence identity with the amino acid sequence of SEQ ID NO: 3.

2. The HMGB1 polypeptide of claim 1, wherein in said HMGB1 polypeptide at least two tyrosine residues corresponding to said positions have been exchanged to amino acid residues independently selected from glutamic acid, glutamine, aspartic acid, and asparagine.

3. The HMGB1 polypeptide of claim 1, wherein in said HMGB1 polypeptide all four tyrosine residues at said positions have been exchanged to glutamic acid residues or have been exchanged to glutamine residues.

4. The HMGB1 polypeptide of claim 1, wherein in said HMGB1 polypeptide all four tyrosine residues at said positions have been exchanged to glutamic acid residues.

5. The HMGB1 polypeptide of claim 1, wherein in said HMGB1 polypeptide all four tyrosine residues at said positions have been exchanged to glutamine residues.

6. The HMGB1 polypeptide of claim 1, wherein said HMGB1 polypeptide comprises an amino acid sequence having at least 95% sequence identity to any one of SEQ ID NOS: 5 to 8.

7. The HMGB1 polypeptide of claim 1, wherein said HMGB1 polypeptide is derived from a human HMGB1 polypeptide.

8. The HMGB1 polypeptide of claim 1, wherein said HMGB1 polypeptide induces increased cell death in cultured SW480 cells at a concentration of 0.8 μM compared to a polypeptide comprising an amino acid sequence of SEQ ID NO:3.

9. A polynucleotide encoding a polypeptide according to claim 1.

10. A method for treating cancer and/or for inducing immune modulation in a subject comprising
 a) contacting said subject with a polypeptide according to claim 1, and, thereby
 b) treating cancer and/or inducing immune modulation in said subject.

11. The method of claim 10, wherein said treating cancer and/or said immune modulation comprises cellular cancer immune therapy.

12. The method of claim 10, wherein said treating cancer and/or said immune modulation comprises inducing TNF-alpha secretion by NK cells.

13. The method of claim 10, wherein said treating cancer and/or said immune modulation comprises avoiding inducing an adverse event.

14. The method of claim 10, wherein said treating cancer and/or said immune modulation comprises avoiding inducing cytokine release syndrome (CRS).

* * * * *